United States Patent [19]

Khan

[11] 4,067,776
[45] Jan. 10, 1978

[54] METHOD FOR DIFFERENTIAL DIAGNOSIS OF MENINGITIS WITH A LIMULUS LYSATE TEST

[75] Inventor: Waheed N. Khan, Potomac, Md.

[73] Assignee: Research Foundation of Children's Hospital, Washington, D.C.

[21] Appl. No.: 635,270

[22] Filed: Nov. 25, 1975

[51] Int. Cl.$^2$ ............................................... C12K 1/04
[52] U.S. Cl. .............................. 195/103.5 M; 195/127
[58] Field of Search .................. 195/103.5 R, 127, 99, 195/103.5 M; 424/95, 101; 23/230 B

[56] References Cited

U.S. PATENT DOCUMENTS

| | | | |
|---|---|---|---|
| 3,704,206 | 11/1972 | Freake et al. | 195/103.5 R |
| 3,876,503 | 4/1975 | Mennen | 195/103.5 R |
| 3,893,892 | 7/1975 | Mehl | 195/127 |
| 3,954,663 | 5/1976 | Yamamoto et al. | 195/99 |

OTHER PUBLICATIONS

Nachum et al "Rapid Detection of Gram-Negative Bacterial Meningitis by the Limulus Lysate Test" The New England J. of Med., vol. 289, (1973) pp. 931-934.
Stumacher et al "Limitations of the Usefulness of the Limulus Assay for Endotoxin" New England J. of Med., vol. 288, (1973) pp. 1261-1264.
Worthington's World, vol. 3, No. 2, (1975) Published by Worthington Biochemical Corporation, Freehold, N. J. 07728.

*Primary Examiner*—Raymond N. Jones
*Assistant Examiner*—C. A. Fan
*Attorney, Agent, or Firm*—Cushman, Darby & Cushman

[57] ABSTRACT

A method for rapid bedside diagnostic differentiation between aseptic meningitis and Gram-negative bacterial meningitis is carried out in a positive control vessel, a negative control vessel and a test vessel, wherein each vessel contains an equal amount of lyophilized limulus lysate and the positive control vessel also contains an amount of lyophilized Gram-negative bacterial endotoxin.

19 Claims, 1 Drawing Figure

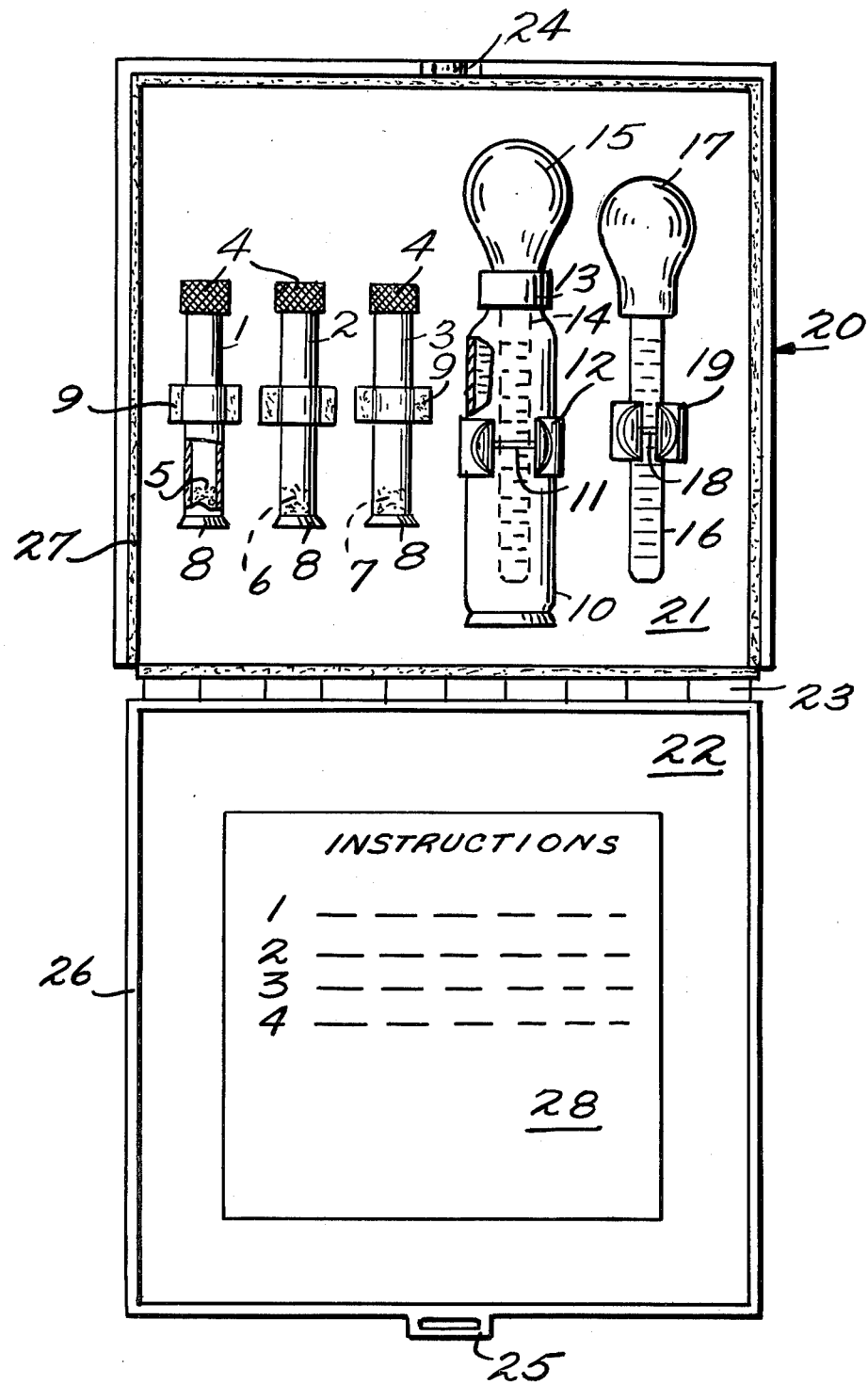

METHOD FOR DIFFERENTIAL DIAGNOSIS OF MENINGITIS WITH A LIMULUS LYSATE TEST

BACKGROUND OF THE INVENTION

As is known in the art, meningitis may be broadly characterized as aseptic meningitis or bacterial meningitis. Aseptic meningitis may refer to two different but related forms of meningitis. Firstly, it may be referring to an acute febrile illness with meningeal irritation and cerebro-spinal fluid (CSF) pleocytosis, but with normal glucose contents and on culture of the CSF no bacterial isolation is obtained. The second form of aseptic meningitis can be characterized by CSF pleocytosis, normal glucose and the absence of organism involvement. This can include not only viral but other infections as well as non-infectious causes. When viral infections of the central nervous system are invovled, these infections may take three different forms. In the first form, there may be no symptoms and only fever and malaise, but the CSF may be abnormal with a lymphocytic pleocytosis. In a second form, the symptoms may be confined to meningeal manifestations, such as fever, headache, vomiting, stiff neck and back and the like. In the third form, referred to as encephalitis, the meningeal symptoms, noted above, may be accompanied by cerebral disorders including alterations of consciousness, personality changes and the like.

Bacterial meningitis may be caused by one or more of several known bacteria. Among the generally accepted bacteria are the Gram-negative bacteria *Neisseria meningitidis, Haemophilus influenzae, Escherichia coli, Salmonella enteridis* (or group B), *Proteus* species (indole positive and negative) and *Pseudomonas arugeniosa,* and the Gram-positive bacteria, *Diplococcus pneumoniae, Streptococcus pyogenes,* and *Straphylococcus aureus.* In bacterial meningitis, clinical indications show brain and meninges involvement. Some of the clinical signs can include fever, headache, stiff neck and vomiting.

Thus, from a clinical observation, it is difficult to tell whether aseptic meningitis or bacterial meningitis is involved, since the clinical symptoms of the different forms of meningitis can be, at least, overlapping in their manifestations. However, the proper treatment for the forms of meningitis vary significantly, and a rapid and positive diagnosis of the form of meningitis is extremely important in the treatment of meningitis. If the meningitis is diagnosed as bacterial meningitis, the more usual therapy involves administration of antibiotics, of specific types, and such administration should be given as promptly as possible once the diagnosis has been established. The prompt commencement of the therapy is fundamental to the more successful treatment of bacterial meningitis.

Accordingly, when clinical symptoms of meningitis are observed, the first diagnostic procedure is that for distinguishing between aseptic meningitis and bacterial meningitis. Unfortunately, however, usually practiced laboratory means of differentiation between bacterial meningitis and aseptic meningitis may be inadequate or even misleading, particularly in distinguishing between bacterial meningitis and viral meningitis. As can be easily appreciated, the ability to make such distinctions is further significantly complicated when antibiotics have been administered to the patient prior to the testing for meningitis, since the antibiotics can substantially attenuate the bacterial infection and/or cause modification of the normal clinical symptoms thereof. It has been found, for example, that the administration of antibiotic thereapy prior to testing CSF for meningitis can cause a decrease of about 25% in the positive results of the CSF culture test and can cause a decrease of about 15% in the positive results of the Gram stain test (in this regard, see Lewis, E. B., "Partially Treated Meningitis," *Am. J. Dis. Child,* 128:145–147, 1974). These tests, therefore, can be totally inadequate to distinguish between aseptic and bacterial meningitis or at least misleading when there has been a prior administration of antibiotics.

It has also been found that tests for CSF pleocytosis, sugar and protein content can be confusing, even when no antibiotic pre-treatment has been given. For example, it has been found that approximately 10% of culture-proved cases of acute bacterial meningitis will exhibit low white cell counts with a predominance of lymphocytes in the CSF. Such findings are more normally associated with the classical characteristics of aseptic meningitis rather than bacterial meningitis. Similar misleading test results have been demonstrated in patients with Haemophilus influenzae meningitis, Neisseria meningitides and Diplococcus pneumoniae meningitis.

Conversely, cases of aseptic meningitis having high pleocytosis, which is more suggestive of a bacterial etiology, may be encountered. This is particularly true with meningitis caused by enteroviruses. Early in the course of Coxsackie and Echo virus meningitis, CSF cell counts may be well over 500 or even 1,000 white cells per cubic milliliter with a predominance of granulocytes. An analysis of cases of patients suffering from Echovirus (type 4) meningitis revealed that 25% of patients had a pleocytosis above 500 white cells per cubic milliliter and 70% had a predominance of granulocytes on the initial tap. Thus, it may be concluded the neither the degree nor the character of CSF pleocytosis is always helpful diagnostically, where the enteroviruses are involved, because of the overlap in the range of values between the "classical" aseptic and bacterial meningitis findings.

Similarly, a CSF sugar content study showed that CSF sugar determinations were normal in 35% of culture-proved cases of bacterial meningitis. Thus, CSF sugar values often lacked reliability as a diagnostic parameter.

In view of the above, the art has had a long-felt need for a more accurate test for distinguishing between aseptic and bacterial meningitis. An important advance in this regard was with the discovery of clot formation of amebocyte lysate from the *Limulus polyhemus* (horseshoe crab) in the presence of minute amounts of endotoxin produced by Gram-negative bacteria (see Leven, J., and Bang, F., "The Role of Endotoxin in the Extracellular Coagulation of Limulus Blood," *Johns Hopkins Med. J.,* 115:265–274, 1965). This has led to proposals for using Limulus lysate in detection of Gram-negative bacteria (see Jorgensen, J., et al, "Rapid Detection of Gram-Negative Bacteriuria By Use of the Limulus Endotoxin Assay," *Applied Microbiology,* Vol. 26, No. 1, (1973) p. 38–42 and Jorgensen, J., Smith, R., "Rapid Detection of Contaminated intravenous Fluids Using the Limulus In Vitro Endotoxin Assay, " *Applied Microbiology, Vol.* 26, No. 4, (1973), p. 521–524). It has also been proposed to use the so-called Limulus lysate test for detection of bacterial meningitis. In one study, positive Limulus lysate assays were obtained on all initial CSF specimens from 38 patients with culture-proved Gram-negative bacterial meningitis. Of these 38 cases, 29 were due to *H. influenzae* and 7 to *N. meningitidis*. No positive Limulus lysate tests were noted in patients with Gram-positive bacterial meningitis, *Tuberculosis meningitis*, aseptic meningitis, or patients without meningitis. Thus, it was concluded that the Limulus lysate assay was a sensitive test for the diagnosis of untreated Gram-negative bacterial meningitis (see Nachum, R., Lipsey, A., and Siegel, S. E., "Rapid Detection of Gram-Negative Bacterial Meningitis by the Limulus Lysate Test, " *New England J. Med.*, 289:931-934, 1973). It should be noted, however, that the reliability of testing Gram-negative bacteria by the Limulus lysate test is not without controversy and the accuracy thereof has been questioned (see Martinez, G. L., Quintiliani, R., and Tilton, R., "Clinical Experience on the Detection of Endotoxinemia With the Limulus Test," *J. Infect. Dis.*, 127:102-105, 1973; Stumacher, R., Kovnat, M., and McCabe, W., "Limitation of the Usefulness of the Limulus Assay for Endotoxin," *New England J. Med.*, 288:1261-1264, 1973; and Feldman, S., and Pearson, T. A., "The Limulus Test and Gram-Negative Bacillary Sepsis," *Am. J. Dis. Child*, 128:172-174, 1974). Nevertheless, it is believed that the Limulus lysate test is the best overall test to distinguish between bacterial meningitis and aseptic meningitis.

The test does suffer, however, from serious difficulties. As can be appreciated from the foregoing, it is of primary importance that the results of any test for distinguishing from aseptic meningitis and bacterial meningitis be made available to the clinician as soon as possible. Significant delays in obtaining the results of such tests can seriously undermine the effectiveness of thereapy instituted after those results are known. The conventional manner of carrying out the Limulus lysate test is described by Nachum et al, cited above. Basically, equal amounts of CSF and lysate are added to pyrogen-free glass culture tubes and incubated in a 37° C water bath for 4 hours. Tubes are observed at 15-minute intervals during the initial incubation period. Tests still negative after the initial 4-hour incubation period are further incubated at room temperature for an additional 20 hours. A definite increase in viscosity and turbidity usually, but not necessarily, progressing to adherent granules or solid gel is interpreted as a positive test. Negative assays remain clear or contain slight flocculent precipitates suspended in clear fluid media. A scale of positive reaction is: negative-clear of slightly flocculated; +— increased turbidity and viscosity; + +— adherent granules; and + + +— solid gel. Thus, the test not only requires laboratory equipment and extended time periods, but the subjective determination of a positive or negative result requires an experienced laboratory technician. This substantially decreases the usefulness of the Limulus lysate test in differentiating between aseptic and bacterial meningitis. It would therefore be of significant advantage in the art to provide a modified Limulus lysate test which can be rapidly carried out with simple equipment, essentially at the bedside, and which does not require an experienced clinician to accurately interpret the test. As can be easily appreciated, experienced clinicians to accurately interpret the conventional test are not readily available to most practicians and an incorrect interpretation of a Limulus lysate test could cause most serious consequences in subsequent treatment for the meningitis.

OBJECTS OF THE INVENTION

It is therefore an object of the present invention to provide a method for rapidly distinguishing between aseptic meningitis and Gram-negative bacterial meningitis. It is a further object of the invention that this method may be carried out, essentially, at the "bedside" and with relatively simple equipment. It is a further object of the invention to provide that method such that the untrained clinician can accurately interpret the results of the test. Other objects will be apparent from the following disclosure and claims.

BRIEF DESCRIPTION OF THE INVENTION

The present invention is a result, primarily, of three main features. The first feature is the discovery that lyophilized limulus lysate may be stored under ambient conditions for long periods of time and can be subsequently re-activated and used in the Limulus lysate test without any substantial decrease in the accuracy of the test. The second feature is the discovery that Gram-negative bacterial endotoxin may be similarly lyophilized and re-activated and that the accuracy of testing re-activated Limulus lysate therewith is not substantially decreased. A third feature is that the degree of clotting and/or turbidity produced by the combination of the lyophilized and re-activated Limulus lysate and lyophilized and re-activated Gram-negative bacterial endotoxin will be substantially constant for standard compositions thereof even after prolonged storage periods of the lyophilized materials and under somewhat varying conditions of reactivation and testing, e.g., temperature and time periods. All of the foregoing have been combined to provide the method of the invention. Additionally, the foregoing has allowed the construction of a portable kit of relatively simple equipment for carrying out the present method.

Briefly stated, the invention provides a method for rapid bedside diagnostic differentiation between aseptic meningitis and Gram-negative bacterial meningitis. According to the method three transparent sterile pyrogen and endotoxin-free closable vessels are provided. The vessels are individually identifiable as a positive control vessel, a negative control vessel and a test vessel. The means of identification may be as desired, such as marking, coloring or labeling. Each of the vessels contains an aliquot of lyophilized Limulus lysate, but in addition, the positive control vessel also contains an aliquot of lyophilized Gram-negative bacteria endotoxin. An aliquot of cerebro-spinal fluid taken from a patient suspected of having meningitis is placed in the test vessel. A volume of pyrogen and endotoxin-free water, which is substantially equal to the volume of the aliquot of cerebro-spinal fluid, is placed into each of the positive control vessel and the negative control vessel. After only a small amount of agitation for mixing, the lyophilized Limulus lysate in each of the vessels and the lyophilized endotoxin in the positive control vessel will be re-activated by virtue of solution in the spinal fluid in the test vessel and by virtue of solution in the water in the control vessels. With re-activation, the reaction between the endotoxin and the Limulus lysate in the positive control vessel will commence. Similarly, Gram-negative bacteria in the spinal fluid of a patient suffering from bacterial meningitis will commence reaction in the test vessel. On the other hand, since no bacteria will be contained in the negative control vessel, the only reaction that will take place will be chemical/- physical reactions that might result from the pyrogen-free water and the Limulus lysate under the particular test conditions, e.g., temperature, specific amounts of agitation, specific volumes, etc. The three vessels are preferably closed immediately or at least within a reasonably short time to avoid contamination, although in a reasonably clean environment this is not required. The vessels are then placed in an environment where the temperature is no more than 45° C. Above such temperature the bacterial action could be substantially attenuated. The vessels are then incubated in an undisturbed manner in the environment for at least 15 minutes and until sufficient bacterial action has taken place that the test results are clear and unambiguous. It is important that the incubation be in a substantially undisturbed manner. After the incubation period, varying degrees of turbidity may be observed in the test vessels. However, to insure that an accurate determination of a positive test is made, all three of the vessels are carefully inverted. The negative control will flow in the nature of a fluid even if some turbidity is present due to test conditions, as explained above, since this negative control has neither the bacteria nor endotoxin to cause clotting of the Limulus lysate. The positive control, if carefully inverted, will retain the rather fragile clot formed by reaction of the endotoxin and Limulus lysate and not flow. The test vessel, therefore, can be further confirmed as either a positive or negative result, depending on whether the carefully inverted test vessel shows flow (negative results) or lack of flow, i.e., a clot (positive results). Thus, the gentle inverting of the vessels is a very valuable confirmation test in addition to the visually observed degree of turbidity in the three vessels.

Thus, the clinician has before him: (1) a negative control where no bacterial action has taken place and any turbidity will be a result of the interaction between the Limulus lysate and the pyrogen-free water under the prevailing test conditions; (2) a positive control where turbidity and clotting have occurred to a relatively known and reproducible degree by reaction of known Gram-negative bacterial endotoxin and the Limulus lysate; and (3) the test vessel. With such side-by-side comparisons and the vessel inverting test, even an unskilled and untrained clinician can determine whether the test vessel shows a positive result or whether any turbidity and lack of clotting is essentially the same as that produced by the interaction of the pyrogen-free water and Limulus lysate, as demonstrated by the negative control. Therefore, a conclusion of a positive or negative test result can be quickly and accurately made without the fear of incorrect interpretation.

The kit of the present invention for carrying out the above test will consist of the three transparent, sterile, pyrogen- and endotoxin-free closable vessels, which vessels are individually identifiable as a positive control, a negative control and a test vessel, and wherein each of the vessels contains the aliquots of lyophilized Limulus lysate and the positive control vessel also contains the aliquot of lyophilized Gram-negative bacterial endotoxin. The kit will also have a container of sterile, pyrogen- and endotoxin-free water for re-activating the Limulus lysate and endotoxin in the control vessels. Sterile, pyrogen- and endotoxin-free transfer means are also provided for individually transferring a measured amount of the water and a cerebro-spinal fluid sample to the respective control vessels and test vessel. Each of the vessels will have a means for positively closing the vessels. This kit allows the proper sample and controls to be prepared. Once these vessels are properly prepared, the incubation may take place, either at room temperature or in a heated environment. That heated environment may be any convenient laboratory oven, water bath or the like. However, the disposable kit discussed above may have therewith a non-disposable heating means for heating the vessels, if desired.

DESCRIPTION OF THE DRAWING

The drawing shows in diagrammatic form the component parts of the kit.

DETAILED DESCRIPTION OF THE INVENTION

The method of the invention will give a rapid bedside diagnostic differentiation between aseptic meningitis and Gram-negative bacterial meningitis. Thus, the test may be carried out in as little as about fifteen minutes, including the times necessary for re-activating the lyophilized Limulus lysate and endotoxin, although more normally the time will require approximately ¾ of an hour to 1½ hours, especially about 1 hour in order to insure a sufficiently long incubation period that the differentiation between positive and negative results will be clear and unequivocal. It will also be appreciated that the test need not be carried out at the "bedside," and this term is to indicate that the test is suitable for being carried out at the locus of the patient and need not be carried out in a laboratory. Thus, the term "bedside" is to be construed in the foregoing manner.

As can be easily appreciated, the vessels used in carrying out the test must be transparent in order that a visual comparison of the clotting and/or turbidity may be made. The vessels need not be transparent over their entire areas, and it is only necessary that a sufficiently large transparent portion be provided to insure that the resultant clotting and turbidity can be observed. Thus, the term "transparent" in this connection is defined to mean at least a transparent portion of the vessel.

The size of the vessels may be entirely as desired, but it is preferred that the vessels be consistent with containing normal spinal fluid sample volumes. For example, test tubes of approximately 10 × 75 mm are suitable in these regards, so long as the tubes are closable. The closing of the tubes need not be in an air-tight manner and a conventional test tube stopper is satisfactory in this regard, although it is preferred that such tubes have a more secure seal, such as a ground glass joint or heat-sealed glass ampule. Alternately, of course, conventional test vials with a screw cap top may be used.

Each of the vessels will contain an aliquot of lyophilized (i.e., freeze dried) Limulus lysate. An aliquot in this context means that the lyophilized Limulus lysate contained in each vessel will be sufficient to provide a potency of the activated (re-dissolved) Limulus lysate that a positive reaction to Gram-negative bacteria can be observed, i.e., substantial turbidity and/or clotting. Thus, the aliquot of Limulus lysate must be proportioned to the expected volume of spinal fluid sample so as to provide a concentration of Limulus lysate in the spinal fluid to give an unequivocal positive reaction if Gram-negative bacteria are present. Of course, for large samples of spinal fluid, the absolute amount of the aliquot will be larger. For convenience, it is preferred that the amount of Limulus lysate in the re-activated condition (either with spinal fluid or water) is such as to provide a potency substantially equal to standardized Limulus lysate. Standardized Limulus lysate is known in the art but may be defined as that concentration of Limulus lysate in the fluid volume that will produce a firm clot when treated with from 0.02 to 0.08 nanograms of standard Klebsiella endotoxin per milliliter of the solution of Limulus lysate (reactivated Limulus lysate in the present case). For tighter control, however, the amount of standard Klebsiella endotoxin per milliliter of Limulus lysate solution should be between 0.04 and 0.06 nanograms.

It should also be understood that the re-activation of the Limulus lysate in the test vessel need not be with spinal fluid alone. Thus, if the amount of spinal fluid is limited, i.e., less than that expected, then an additional volume of pyrogen- and endotoxin-free water may be added to the spinal fluid in order to provide the re-activated Limulus lysate at the desired concentration. Indeed, for some purposes, it is more convenient to dilute the spinal fluid with such water, since this can simplify handling of the sample. However, the volume ratio of the water to the spinal fluid will normally be between 0.05:1 and 1:0.1. Aside from the convenience and aside from the lack of adequate sample, the test will normally be carried out with the Limulus lysate in the test vessel being re-activated by the addition of cerebrospinal fluid, alone.

If desired, however, the amount of Limulus lysate in the re-activated solution need not be substantially equal to the standard Limulus lysate solution, but may vary from as little as 0.01 to as much as 0.8 milligrams per milliliter of re-activated solution.

Similarly, the aliquot of lyophilized (i.e., freeze-dried) Gram-negative bacteria in the positive test vessel will be consistent with producing a firm clot in a standardized solution of Limulus lysate. Here again, the absolute amount of lyophilized endotoxin in the positive test vessel will vary with the expected re-activated volume in the positive test vessel. While any known Gram-negative bacterial endotoxin may be used in the positive test vessel, e.g., that derived from the above-mentioned meningitidis producing bacteria, it is more convenient to use Klebsiella endotoxin since this corresponds with the same endotoxin used for standardizing the Limulus lysate. However, for purposes of carrying out the test, it is only necessary that the Gram-negative bacteria be reactive toward the Limulus lysate and this function can, of course, be quite easily and conveniently carried out by simple testing with a standard solution of Limulus lysate.

It should be appreciated that an important feature of the invention is the provision of the above-described fully prepared but inactivated mixture of Limulus lysate and Gram-negative bacterial endotoxin. Thus, there is no requirement for further standardizing the positive control vessel ingredients or for further measuring amounts of ingredients or for performing any further steps in that regard. The positive control is fully prepared. On the other hand, the potentially rapid reaction between the endotoxin and Limulus lysate in the positive control vessel ingredients has been substantially completely prevented. This not only allows the initial mixing of these potentially rapid reacting ingredients, but the long term storage of the mixture without slow reaction which would give a seriously deteriorated test accuracy. This very important feature is provided by the completely and quickly produced lyophilized Limulus lysate and Gram-negative bacterial endotoxin. If these ingredients are mixed prior to lyophilization, the freezing and drying under vacuum (lyophilization) must be rapid, i.e., at least freezing to at least 0° C. within 10 minutes. Of course, if the ingredients are separately lyophilized and then mixed, this rapid lyophilization is not so critical.

As noted above, the incubation after re-activation should not be at a temperature greater than 45° C., but on the other hand, lower temperatures will slow down the reaction between the bacteria (or bacterial products) and the Limulus lysate and extend the required incubation period. Thus, lower temperatures, e.g., below 15° C. should be avoided and preferably the incubation temperature should be closer to body temperature, e.g., at least 30° C. More conveniently, the incubation is at about body temperature, i.e., 37° C. Within the above preferred ranges of temperature, the incubation time will normally be within ½ hour to 3 hours, but will usually be less than 2 hours.

For convenience, the three vessels should be easily identifiable as the negative control vessel, the positive control vessel and the test vessel. Any desired means of positive identification may be used. For example, the vessels may be color coded or labeled by attaching labels, etching or any other marking. Alternately, the vessels may be in different shapes or sizes to identify the vessels. For example, the negative control vessel could be a rectangular cross-sectioned vessel, while the positive control vessel could be a square cross-sectioned vessel and the test vessel could be a circular cross-sectioned vessel, or the base thereof could be so configured. Alternately, an inert coloring material such as dye or tint may be disposed in the three vessels so that upon re-activation, the colors of the fluids in the respective vessels will identify those vessels. For example, the positive control vessel could have a red color therein, the negative control vessel could have a yellow color therein and the test vessel could have a green color therein.

A very surprising and unexpected result in the present invention is the discovery that the re-activated Limulus lysate, prepared according to the present invention, is not affected by the prior treatment of the patient with antibiotics. While not bound by theory, it appears that the present lyophilized Limulus lysate, when re-activated as above, is so sensitive that it can provide accurate results in the presence of either the Gram-negative meningitis producing bacteria or the bacterial products of those bacteria, or both. Accordingly, even if the meningitis-producing bacteria have been substantially killed or retarded by action of a pre-administered antibiotic, the present test is sensitive enough to give accurate results when reacting, alone, with the Gram-negative meningitis-producing bacterial products (primarily the endotoxin).

The drawing shows a kit suitable for the bedside administration of the test. As can be seen, the kit is a portable, self-contained kit. In the kit are three transparent, sterile, pyrogen- and endotoxin-free closed vessels, designated as vessels 1, 2 and 3. The vessels are shown with screwed tops 4 for closing the vessel. However, any form of vessel may be used, e.g., heat-sealed glass ampules, either round or flat-bottomed. As illustrated, vessel 1 is the positive control vessel and contains a combination of lyophilized Limulus lysate and lyophilized Gram-negative bacteria endotoxin indicated by 5. Vessel 2 is the negative control vessel and contains only lyophilized Limulus lysate, designated by 6, and, correspondingly, lyophilized Limulus lysate 7 is contained in test vessel 3. These vessels have bases 8 which bases are color coded so that the vessels are identifiable as designated above. The vessels will be held in the kit by restraining straps 9. These straps are made in such a manner that the vessel can be removed from the kit only by breaking the strap. This will be a positive indication that the vessels had been previously used and are not to be used again.

Similarly disposed in the kit is a container of sterile, pyrogen- and endotoxin-free water 10 and is also held in the kit by a breakable strap 11 and a supporting clamp 12. The container has a screwed top 13 which has disposed therethrough a graduated pipette 14 which is activated by suction bulb 15. This graduated pipette allows transferring of a measured amount of the water from the container to the vessels. Also in the kit is a sterile, pyrogen- and endotoxin-free graduated pipette 16 actuated by a suction bulb 17, which may be used in transferring a sample of the spinal fluid to the test vessel. Here again, the graduated pipette will be held by breakable strap 18 and a supporting clamp 19.

The foregoing components of the kit will be made of relatively inexpensive and disposable material so that the kit may be economically used only once. For example, the pipettes and vessels may be made of relatively inexpensive glass or plastic so long as the glass and plastic may be sterilized and rendered pyrogen- and endotoxin-free.

The components of the kit will be disposed within a self-contained carrying case 20 which may have a lower portion 21 and an upper portion 22. The upper portion is connected to the lower portion via a hinge 23 so that the upper portion may be folded onto the lower portion and latched via tongue and groove latch 24/25 to close the container. A seal may be provided by a projection 26 that fits into a gasket 27 for receiving that projection and thus providing a relatively tight seal. The seal may, indeed, have a glue disposed thereon such that once the case is closed, an opening of the case will tear the seal and clearly show that the case has been previously opened. Of course, a previously opened case will not be used in a test. Contained in the upper portion of the case can be a set of instructions 28 which detail the manner in which the test with the components is to be conducted. Additionally, while not required, the entire case may be disposed in a sealed plastic bag, and indeed the entire case and contents may be terminally sterilized, if desired.

As an alternate to the bulb and pipette in the container of water, the screwed top of the container may be shaped into a pouring spout (not shown) so that predictable pouring from the container is possible. In this embodiment, the container will then be marked with graduations (not shown) so that a measured amount of the water may be poured from the container. Preferably, however, the transfer means is the pipette shown in the drawing.

If desired, a portable heating means, such as an electrically heated block with a thermostatic control may be provided. This would not be a disposable item but could be available, for example, within wards of a hospital, for heating the vessels during the incubation step. The block would have indentations or holes therein for receiving and holding each of the vessels in an undisturbed manner and be capable of heating and maintaining the vessels to a controlled temperature, generally between 30° C. and 40° C., more preferably the block will be pre-set for maintaining the temperature at body temperature, i.e., 37° C.

The invention will be further illustrated by the following examples but it is to be clearly understood that the invention is not limited thereto but extends to the breadth of the foregoing disclosure. In the examples, all proportions are by weight, unless otherwise designated.

EXAMPLE

Material and Methods

In this test 335 patients were included. For every patient, a lumbar puncture was performed because of suspected meningitis.

Samples of CSF for the Limulus lysate assays were collected by standard clinical procedures which are well known to the clinical arts. The collected samples were stored in sterile pyrogen-free plastic tubes. On each spinal fluid, a routine cell count, Gram stain and culture were performed together with a determination of protein, sugar and LDH levels. All glassware, pipettes, bottles and test tubes used in the tests were rendered endotoxin-free by pre-heating at 180° C. for at least 3 hours.

The sensitivity of each batch of Limulus lysate to be used in the tests was determined by titrating with standard Klebsiella endotoxin. The Limulus lysate batches ranged in sensitivity to endotoxin from 0.04 to 0.06 ng/ml and produced a firm clot in the presence of these low concentrations. The Klebsiella endotoxin standard was obtained in lyophilized form (as lipoplysaccharide) from the Bureau of Biologics, Food and Drug Administration, Bethesda, Maryland, in a 1.0 mcg/ml concentration. This endotoxin was diluted to 100 ng/ml and kept as stock concentrations of endotoxin in a frozen state of −70° C. A working dilution of 1.0 ng/ml was made for daily use; for performing titrations, further two-fold dilutions were made ranging from 1.0 ng/ml to 0.001 ng/ml.

As a control, tests were conducted by trained laboratory technicians using laboratory equipment. In these control tests, the Limulus lysate test was performed by using pre-standardized Limulus lysate in a 0.1 ml volume in 10 × 75 mm pyrogen-free test tubes, mixing it with an equal amount of spinal fluid (0.1 ml). Both positive and negative control tests were included each time a CSF sample was tested. One tube (10 × 75 mm) containing 0.1 ml of Limulus lysate and 0.1 ml of pyrogen-free water constituted a negative control. A similar tube contained 0.1 ml of Limulus lysate and 0.1 ml of Klebsiella endotoxin (0.1 ng/ml concentration) and constituted a positive control. All these tubes were incubated at 37° C. in a hot water bath for 1 hour and care was taken not to disturb the tubes.

In a corresponding bedside test, a kit was prepared that consisted of three tubes, each containing premeasured lyophilized test material ready to be used. Each tube contained the equivalent of 0.1 ml of standardized Limulus lysate in lyophilized form. These tubes were color coded red, yellow and green. The red tube in addition contained the equivalent of 0.1 ng/ml of Klebsiella endotoxin and was the positive control tube. Each time a sample of spinal fluid was to be tested, this set of three tubes was utilized. Employing this bedside technique, the Limulus lysate test on CSF was performed by house officers and medical students minutes after the lumbar tap was done. To the red (positive control) and yellow (negative control) tubes of the test kit, 0.2 ml of pyrogen-free water was added with a pyrogen-free lambda capillary pipette and mixed well until the contents dissolved completely. All pyrogen-free water was initially checked for endotoxin against standardized Limulus lysate. This is of importance since each batch of water can vary and even trace amounts of endotoxin can produce false positive reactions. To the green tube, 0.1 ml of pyrogen-free water and 0.1 ml of the patient's CSF were added with similar pipettes and mixed well. All three tubes were then incubated in a heat block set at 37° C. for 1 hour. Care was taken not to disturb the tubes during incubation.

The interpretation of the Limulus test, whether performed at the bedside or in the laboratory was the same. After 1 hour, the test tubes were picked up individually and gently inverted 180°. The red coded tube had a solid clot, appeared turbid and the clot did not break on total inversion (positive control). The yellow coded tube did not have a clot and was clear and free-flowing (negative control). In the green coded tube (which was the patient's CSF being tested) the presence of a solid clot indicated a positive Limulus lysate test, meaning a Gram-negative bacterial infection or bacterial end-products in the spinal fluid. If there was no clot formation of the Limulus lysate in the green tube, the test was negative and the CSF was free of Gram-negative bacteria or bacterial end-products.

RESULTS

The results of the assays are summarized in Table I. As will be noted, positive Limulus lysate tests were obtained within 1 hour in 33 of 34 cases of *H. influenzae* meningitis; four additional patients with Gram-negative meningitis including two cases due to *N. meningitidis*, one Pseudomonas and one Klebsiella also showed positive Limulus lysate tests. Conversely, 13 patients with Gram-positive bacterial meningitis all yielded negative Limulus assays, as expected. These included six cases due to *D. pneumoniae,* four due to Group B Streptococcus, one caused by Group A Streptococcus and one each to *Staphylococcus aureus* and *Staphylococcus epidermidis*. Similarly, as anticipated, all 48 cases of aseptic meningitis and 236 patients with no meningitis showed negative Limulus lysate tests.

TABLE I
RESULTS OF THE LIMULUS TEST ON CSF SPECIMENS

| Diagnosis | Number of Patients | Patients With Positive Limulus Test |
|---|---|---|
| *H. influenzae* meningitis | 34 | 33 (97%) |
| *Neisseria meningitidis* meningitis | 2 | 2 (100%) |
| *Klebsiella* meningitis | 1 | 1 (100%) |
| *Pseudomonas* meningitis | 1 | 1 (100%) |
| *Diplococcus pneumoniae* meningitis | 6 | 0 (0%) |
| *Streptococcus* meningitis (Group B) | 4 | 0 (0%) |
| *Streptococcus* meningitis (Group A) | 1 | 0 (0%) |
| *Staphylococcus aureus* meningitis | 1 | 0 (0%) |
| *Staphylococcus epidermidis* meningitis | 1 | 0 (0%) |
| Aseptic meningitis | 48 | 0 (0%) |
| No meningitis | 236 | 0 (0%) |
| TOTAL | 335 | |

A comparison of the Limulus lysate tests and Gram stain smears on initial spinal fluid samples is summarized in Table II. A total of 38 patients with Gram-negative meningitis yielded a positive Limulus lysate test in 37 cases (97%), while only 71% showed organisms on smear of the spinal fluid.

In this series, 10 of 34 cases of *H. influenzae* meningitis had received prior antibiotic treatment (ampicillin in 9 of the 10 cases) and except for one patient, all these pre-treated cases showed positive Limulus lysate tests.

In the majority of the patients with a positive Limulus lysate test the response to early treatment was so good that the patients tested negative within 48 to 72 hours of commencement of treatment. A rapid return to a negative Limulus assay was prognostically encouraging. In those few cases where the Limulus lysate test remained positive even after several days of treatment, the course of the disease was often more stormy and the morbidity higher. Thus, the test can also be used for prognostic purposes.

TABLE II
COMPARISON OF LIMULUS ASSAY AND GRAM STAIN ON INITIAL SPINAL FLUID SPECIMENS

| Organism | Number of Patients | Patients With Positive Limulus Assay | Patients with Positive Gram Stains |
|---|---|---|---|
| *H. Influenzae* | 34 | 33 | 23 |
| *Neisseria meningitides* | 2 | 2 | 2 |
| *Klebsiella* | 1 | 1 | 1 |
| *Pseudomonas* | 1 | 1 | 1 |
| TOTALS | 38 | 37 (97%) | 27 (71%) |

The bedside technique of the Limulus lysate test proved to be as reliable as the quality control test performed in the laboratory.

The results show that the present Limulus lysate test is a valuable, predictable and reliable test in the rapid diagnosis of Gram-negative bacterial meningitis. Out of 335 patients tested, only one false negative and no false positive assays have been observed. (The false result was due to factors beyond the clinical control.) It is also emphasized that 10 of 34 cases of *H. influenzae* meningitis had received prior antibiotic treatment and all of these pre-treated cases showed positive Limulus lysate tests. Thus, prior antibiotic therapy in no way compromised the validity of the present Limulus lysate test in differentiating between Gram-negative bacterial meningitis and aseptic meningitis.

Hitherto, the CSF Limulus lysate test has been a procedure performed only in the laboratory. However, because of its extreme simplicity, the present invention may be practiced at the bedside with only a modicum of instruction, and house staff or medical students were capable of performing the test on wards at the time of a lumbar puncture. The advantages of the bedside technique are manifest. In the first place, a definitive answer regarding Gram-negative bacterial or aseptic meningitis is available to the house staff within 1 hour after performing the spinal tap. This allows a quick decision to be made whether to initiate antibiotic therapy or to withhold it. Performance of the Limulus lysate test by the house staff at the bedside further permits a rapid and reliable answer to be obtained at night and on weekends. In this regard, few hospital laboratories have reliable 24-hour-a-day, 7-day-a-week capabilities; this is particularly true with community hospitals.

Having thus described the invention, it will be apparent to those skilled in the art, that various modifications thereof may be practiced. Such apparent modifications are intended to be within the spirit and scope of the following claims.

What is claimed is:

1. A method for rapid bedside diagnostic differentiation between aseptic meningitis and Gram-negative bacterial meningitis comprising:
    1. providing three transparent sterile, pyrogen- and endotoxin-free closable vessels, the three vessels being individually identifiable as a positive control vessel, a negative control vessel and a test vessel, wherein each vessel contains an equal amount of lyophilized Limulus lysate and the positive control vessel also contains an amount of lyophilized Gram-negative bacterial endotoxin, said lyophilized lysate and endotoxin being inactive and essentially unreacted but being capable of reactivation upon the addition of water and/or cerebo-spinal fluid thereto;
    2. placing cerebro-spinal fluid in the test vessel and pyrogen- and endotoxin-free water into each of the positive control vessel and the negative control vessel;
    3. placing the three vessels in an environment at a temperature of between 15° C and 45° C;
    4. incubating the three vessels in an undistrubed manner in the environment for at least 15 minutes so as to reactivate the Limulus lysate for reaction with the endotoxin in the positive control vessel and with any endotoxin in the test vessel; and
    5. inverting each vessel, whereby the degree of the resulting clotting and/or turbidity in the test vessel may be visually compared with that in the positive control vessel and negative control vessel and a test result can be concluded from the comparison, the amount of lyophilized Limulus lysate contained in the re-activated condition being such that will produce a firm clot when treated with from 0.02 to 0.08 ng of standard Klebsiella endotoxin per ml of re-activated Limulus lysate.

2. The method of claim 1 wherein the endotoxin in the positive control vessel is standard Klebsiella endotoxin in the amount of 0.04 to 0.06 ng per ml of re-activated Limulus lysate.

3. The method of claim 1 wherein the Limulus lysate in the test vessel is re-activated by the addition of both pyrogen- and endotoxin-free water and cerebro-spinal fluid.

4. The method of claim 3 wherein the volume ratio of the water to the fluid is between 0.05:1 to 1:0.1.

5. The method of claim 1 wherein the Limulus lysate in the test vessel is re-activated by the addition of only cerebro-spinal fluid.

6. The method of claim 1 wherein the Gram-negative bacterial endotoxin is standardized Klebsiella endotoxin.

7. The method of claim 1 wherein the temperature in step (3) is at least 30° C.

8. The method of claim 7 wherein the temperature is about 37° C.

9. The method of claim 1 wherein the incubation time is at least ½ hour and up to 3 hours.

10. The method of claim 9 wherein the incubation time is less than 2 hours.

11. The method of claim 1 wherein the three vessels are identifiable by one or more of size, shape, color, markings or inert coloring material disposed in the vessels.

12. A portable self-contained kit for the bedside diagnostic differentiation between aseptic meningitis and Gram-negative bacterial meningitis comprising:
    1. three transparent sterile, pyrogen- and endotoxin-free closable vessels, the three vessels being individually identifiable as a positive control vessel, a negative control vessel and a test vessel, wherein each vessel contains an equal amount of lyophilized Limulus lysate and the positive control vessel also contains an amount of lyophilized Gram-negative bacterial endotoxin, said lyophilized lysate and endotoxin being inactive and essentially unreacted but being capable of reactivation upon the addition of water and/or cerebro-spinal fluid thereto;
    2. a container of sterile, pyrogen- and endotoxin-free water;
    3. sterile, pyrogen- and endotoxin-free transfer means for individually transferring a measured amount of the said water and a measured amount of a cerebro-spinal fluid sample to the said control vessels and test vessel, respectively; and
    4. means for closing the said vessels, the amount of lyophilized Limulus lysate contained in the re-activated condition being such that will produce a firm clot when treated with from 0.02 to 0.08 ng of standard Klebsiella endotoxin per ml of re-activated Limulus lysate.

13. The kit of claim 12 wherein each component is made of disposable materials so that the kit is used only once.

14. The kit of claim 12 disposed within a self-contained carrying case.

15. The kit of claim 14 having a seal thereon which must be broken to open the said case.

16. The kit of claim 12 wherein the transfer means for the water is a pouring spout on the container and the container has graduated markings thereon for transferring the measured amount of water.

17. The kit of claim 12 wherein the transfer means is a pipette.

18. The kit of claim 12 which also includes a heating means for receiving and holding each of the said vessels in an undisturbed manner and is capable of heating the vessels to and maintaining the vessels at a controllable temperature of 30° C to 40° C.

19. The kit of claim 18 wherein the heating means is preset for a temperature of about 37° C.

* * * * *